(12) United States Patent
Morita

(10) Patent No.: US 10,307,045 B2
(45) Date of Patent: Jun. 4, 2019

(54) ENDOSCOPE OPTICAL SYSTEM UNIT

(71) Applicant: OLYMPUS CORPORATION, Hachioji-shi, Tokyo (JP)

(72) Inventor: Kazuo Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/675,229

(22) Filed: Aug. 11, 2017

(65) Prior Publication Data
US 2017/0332890 A1    Nov. 23, 2017

Related U.S. Application Data

(63) Continuation of application No. PCT/JP2016/078259, filed on Sep. 26, 2016.

(30) Foreign Application Priority Data

Oct. 1, 2015    (JP) .................. 2015-195956

(51) Int. Cl.
*A61B 1/00*    (2006.01)
*A61B 1/06*    (2006.01)
(Continued)

(52) U.S. Cl.
CPC ........ *A61B 1/0684* (2013.01); *A61B 1/00096* (2013.01); *A61B 1/00163* (2013.01);
(Continued)

(58) Field of Classification Search
CPC ............ A61B 1/00094; A61B 1/00117; A61B 1/00126; A61B 1/0016; A61B 1/00163;
(Continued)

(56) References Cited

U.S. PATENT DOCUMENTS 3,880,148 A    4/1975   Kanehira et al.
3,994,557 A    11/1976  Hopkins
(Continued)

FOREIGN PATENT DOCUMENTS

JP    49053847 A    5/1974
JP    50055348 A    5/1975
(Continued)

OTHER PUBLICATIONS

International Preliminary Report on Patentability (IPRP) dated Apr. 12, 2018 issued in counterpart International Application No. PCT/JP2016/078259.
(Continued)

*Primary Examiner* — Ryan N Henderson
(74) *Attorney, Agent, or Firm* — Holtz, Holtz & Volek PC

(57) ABSTRACT

An endoscope optical system unit includes an endoscope illuminating optical system and an endoscope objective optical system. The endoscope illuminating optical system includes a light-emitting section and a first optical-path deflecting prism group, which includes a first prism, a second prism, and a third prism. The endoscope objective optical system includes a lens group and a second optical-path deflecting prism group, which includes a fourth prism, a fifth prism, and a sixth prism. A direction of irradiation of illumination light by the endoscope illuminating optical system, and a visual field direction of the endoscope objective optical system, are variable by rotation of the prisms.

3 Claims, 17 Drawing Sheets

(51) Int. Cl.
*A61B 1/07* (2006.01)
*G02B 17/04* (2006.01)
*G02B 23/10* (2006.01)
*G02B 23/24* (2006.01)
*G02B 23/26* (2006.01)

(52) U.S. Cl.
CPC ...... *A61B 1/00174* (2013.01); *A61B 1/00183* (2013.01); *A61B 1/06* (2013.01); *A61B 1/0653* (2013.01); *A61B 1/0669* (2013.01); *A61B 1/07* (2013.01); *G02B 17/04* (2013.01); *G02B 23/243* (2013.01); *G02B 23/26* (2013.01); *G02B 23/10* (2013.01); *G02B 23/2469* (2013.01)

(58) Field of Classification Search
CPC ............ A61B 1/00165; A61B 1/00167; A61B 1/0017; A61B 1/00172; A61B 1/00174; A61B 1/00177; A61B 1/00179; A61B 1/00181; A61B 1/00183; A61B 1/00186; A61B 1/00188; A61B 1/0019; A61B 1/00193; A61B 1/00195; A61B 1/00197; A61B 1/002; A61B 1/04; A61B 1/041; A61B 1/042; A61B 1/043; A61B 1/045; A61B 1/05; A61B 1/051; A61B 1/053; A61B 1/055; A61B 1/06; A61B 1/0607; A61B 1/0615; A61B 1/0623; A61B 1/063; A61B 1/0638; A61B 1/0646; A61B 1/0653; A61B 1/0661; A61B 1/0669; A61B 1/0676; A61B 1/0684; A61B 1/0692; A61B 1/07; G02B 23/2407; G02B 23/2423; G02B 23/243; G02B 23/2415; G02B 23/2438; G02B 23/2446; G02B 23/2453; G02B 23/2461; G02B 23/2469; G02B 23/26; G02B 17/04; H04N 5/2259
See application file for complete search history.

(56) References Cited

U.S. PATENT DOCUMENTS

| | | |
|---|---|---|
| 6,560,013 B1 | 5/2003 | Ramsbottom |
| 7,221,522 B2 | 5/2007 | Tesar et al. |
| 8,684,915 B2 | 4/2014 | Katakura |

FOREIGN PATENT DOCUMENTS

| | | |
|---|---|---|
| JP | 50141347 A | 11/1975 |
| JP | 09061722 A | 3/1997 |
| JP | 2003510119 A | 3/2003 |
| JP | 2006204924 A | 8/2006 |
| JP | 4458211 B2 | 4/2010 |
| WO | 2012081349 A1 | 6/2012 |

OTHER PUBLICATIONS

International Search Report (ISR) and Written Opinion dated Nov. 8, 2016 issued in International Application No. PCT/JP2016/078259.
Chinese Office Action (and English language translation thereof) dated Jan. 24, 2019 issued in counterpart Chinese Application No. 201680010944.4.

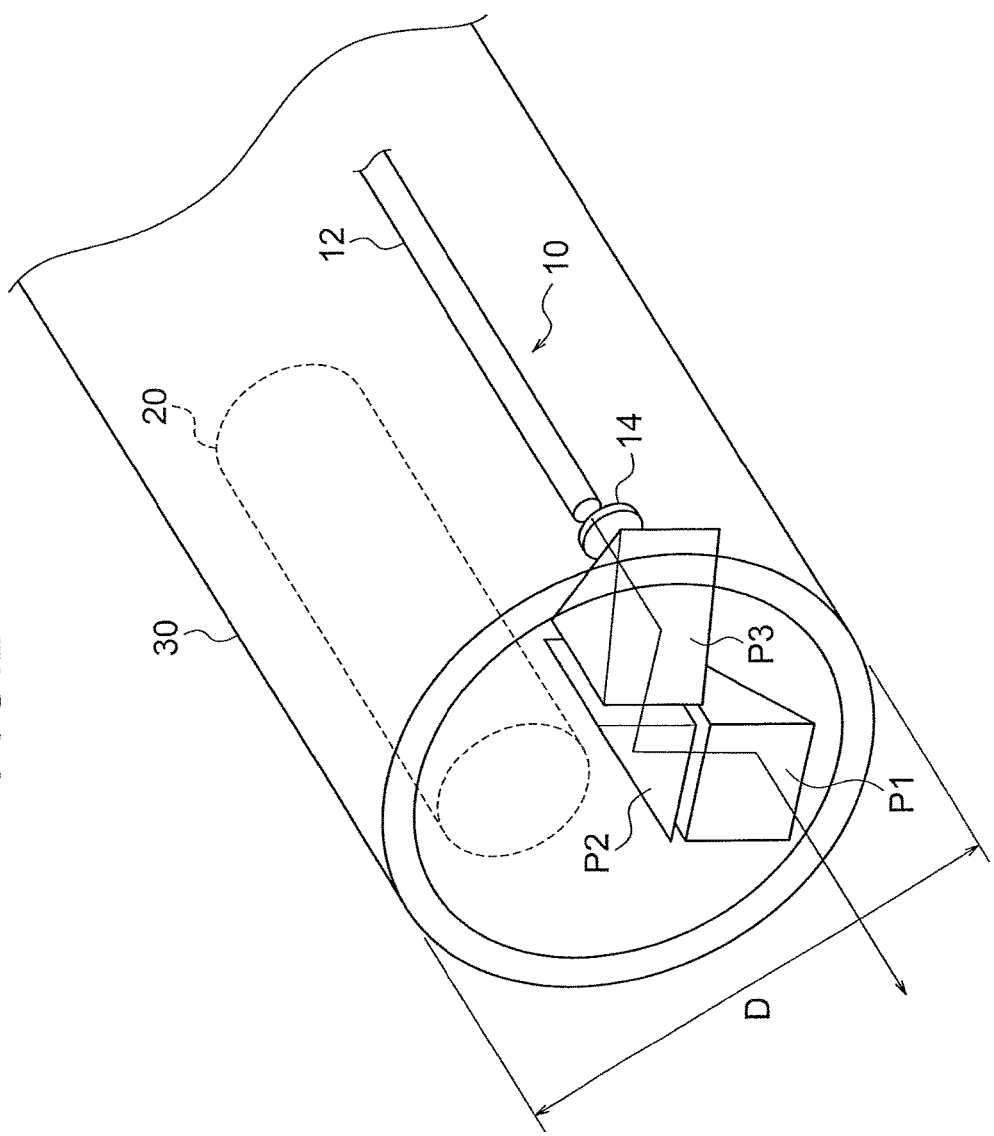

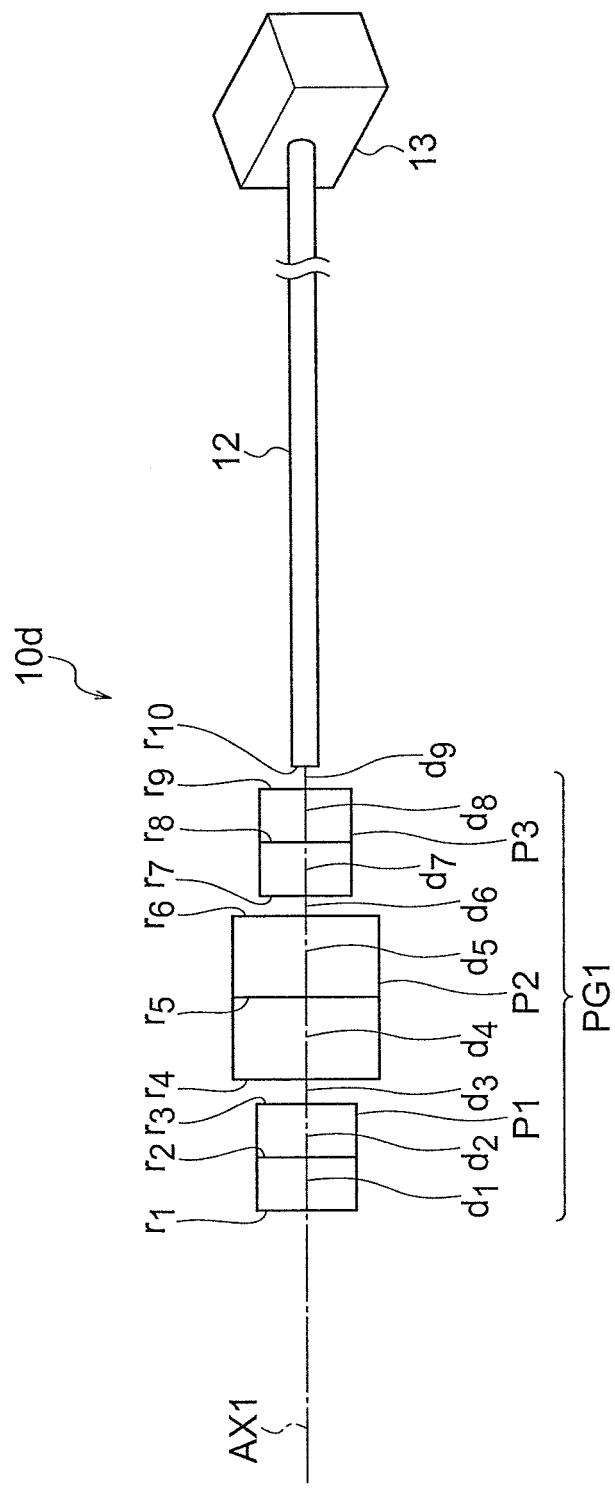

ENDOSCOPE OPTICAL SYSTEM UNIT

CROSS-REFERENCE TO RELATED APPLICATION

The present application is a continuation application of PCT/JP2016/078259 filed on Sep. 26, 2016 which is based upon and claims the benefit of priority from Japanese Patent Application No. 2015-195956 filed on Oct. 1, 2015; the entire contents of which are incorporated herein by reference.

BACKGROUND OF THE INVENTION

Field of the Invention

The present invention relates to an endoscope optical system unit.

Description of the Related Art

An endoscope is an apparatus that has been used widely in a medical field and an industrial field. Particularly, in the medical field, images of various parts inside a body cavity are captured by an endoscope inserted into the body cavity. A diagnosis of a part observed, is carried out by these images. In such manner, endoscopes have been used for observation and diagnosis of various body parts inside the body cavity.

A non-bending variable visual-field endoscope in which it is possible to change a direction of observation by driving an optical element at an interior of an objective optical system without bending an inserting section at the time of observing various parts inside the body cavity, has been known.

In the observation by such variable visual-field endoscope, it is desirable that a subject image in any direction of observation that can be achieved in the objective optical system can be observed with adequate brightness.

Illuminating in advance, regions in all directions of a range of variable visual-field for fulfilling the requirement may be taken into consideration. However, a range to be illuminated being wide, it is difficult to illuminate with uniform intensity in all directions. As a result, problems such as change in the brightness of subject according to the visual-field direction and uneven brightness in the subject image arise.

As another arrangement for fulfilling the requirement, an illuminating optical system proposed in Japanese Patent No. 4458211 Publication for example, has been known. In the illuminating optical system of Patent Literature 1, by making it possible to drive one optical element at an interior of the illuminating optical system, irradiation of illumination light followed by the movement of the objective optical system in the visual-field direction is made possible. With this arrangement, it is possible to illuminate uniformly in any visual-field direction, and furthermore, since it is possible to narrow a range to be illuminated at a time, the unevenness in brightness of a subject image is not susceptible to occur.

SUMMARY OF THE INVENTION

An endoscope optical system unit according to the present invention, comprises, an endoscope illuminating optical system which includes, a light-emitting section, and a first optical-path deflecting prism group which takes in illumination light emitted from the light-emitting section, and irradiates light to a subject upon deflecting an optical path, and the first optical-path deflecting prism group includes three prisms in order from a subject side which are, a first prism, a second prism, and a third prism, and the first prism, the second prism, and the third prism are disposed to be mutually adjacent, and a direction of irradiation of the illumination light is let to be variable to a first direction by rotationally moving the first prism with respect to the second prism, and the direction of irradiation of the illumination light is let to be variable to a second direction which differs from the first direction, by rotationally moving the first prism and the second prism integrally, with respect to the third prism; and an endoscope objective optical system, wherein the endoscope objective optical system includes a second optical-path deflecting prism group, and a lens group, and the second optical-path deflecting prism group includes three prisms in order from the subject side which are, a fourth prism, a fifth prism, and a sixth prism, and the fourth prism, the fifth prism, and the sixth prism are disposed to be mutually adjacent, and a visual field direction is let to be variable to the first direction by rotationally moving the fourth prism with respect to the fifth prism, and the visual field direction is let to be variable to the second direction which differs from the first direction, by rotationally moving the fourth prism and the fifth prism integrally, with respect to the sixth prism, and the first optical-path deflecting prism group and the second optical-path deflecting prism group are disposed such that a third axis of rotation when the fourth prism rotates with respect to the fifth prism, and a first axis of rotation when the first prism of the endoscope illuminating optical system rotates with respect to the second prism, become coaxial, and the first optical-path deflecting prism group and the second optical-path deflecting prism group are disposed such that a fourth axis of rotation when the fourth prism and the fifth prism rotate integrally with respect to the sixth prism, and a second axis of rotation when the first prism and the second prism rotate integrally with respect to the third prism, become coaxial, and both the visual field direction of the endoscope objective optical system and the direction of irradiation of the illumination light of the endoscope illuminating optical system are let to be variable to the first direction by rotationally moving the first prism and the fourth prism integrally, and furthermore, both the visual field direction of the endoscope objective optical system and the direction of irradiation of the illumination light of the endoscope illuminating optical system are let to be variable to the second direction by rotationally moving the first prism and the second prism, and the fourth prism and the fifth prism integrally.

BRIEF DESCRIPTION OF THE DRAWINGS

FIG. 2 is a diagram showing an arrangement in perspective view of an endoscope illuminating optical system according to a second embodiment;

FIG. 9A is a diagram showing an arrangement in cross-sectional view of an endoscope optical system unit according to an example 2;

DETAILED DESCRIPTION OF THE INVENTION

Figure 1A:
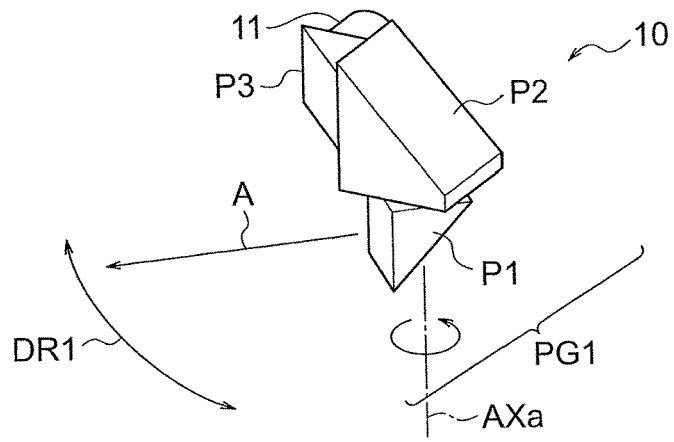
FIG. 1A is a diagram showing an arrangement in perspective view of an endoscope illuminating optical system according to a first embodiment.
Figure 1B:
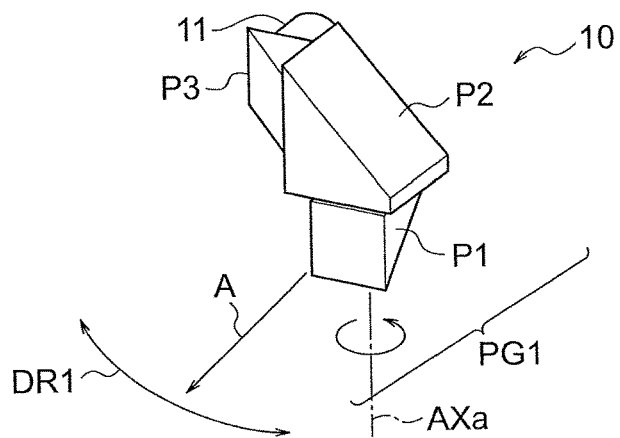
FIG. 1B is another diagram showing an arrangement in perspective view of the endoscope illuminating optical system according to the first embodiment.
Figure 1C:
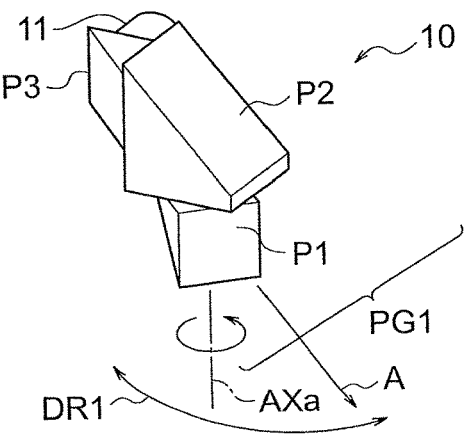
FIG. 1C is still another diagram showing still an arrangement in perspective view of the endoscope illuminating optical system according to the first embodiment.
Figure 1D:
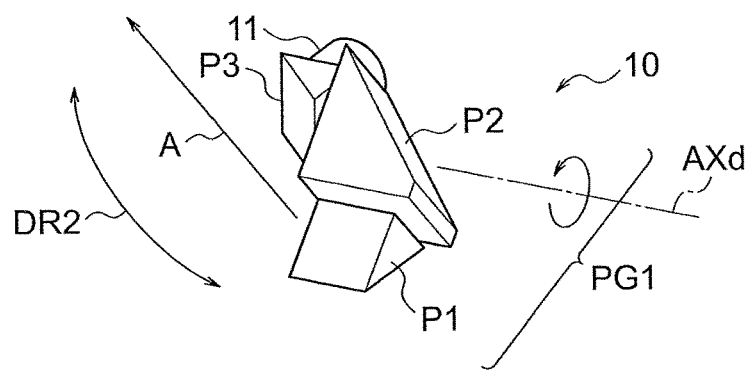
FIG. 1D is still another diagram showing an arrangement in perspective view of the endoscope illuminating optical system according to the first embodiment.
Figure 1E:
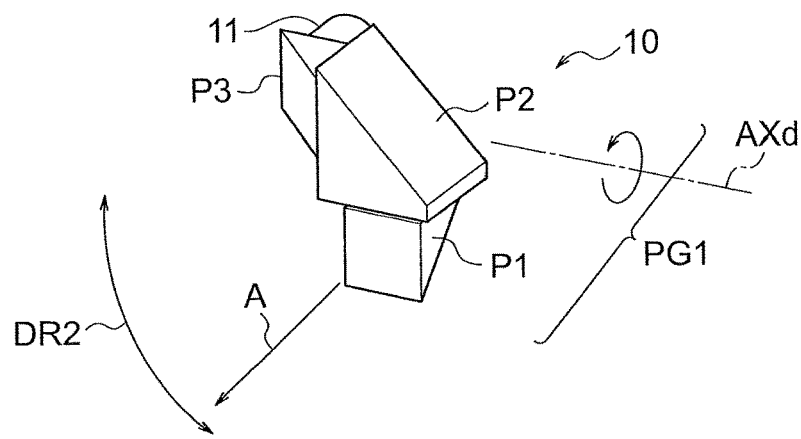
FIG. 1E is still another diagram showing an arrangement in perspective view of the endoscope illuminating optical system according to the first embodiment.
Figure 1F:
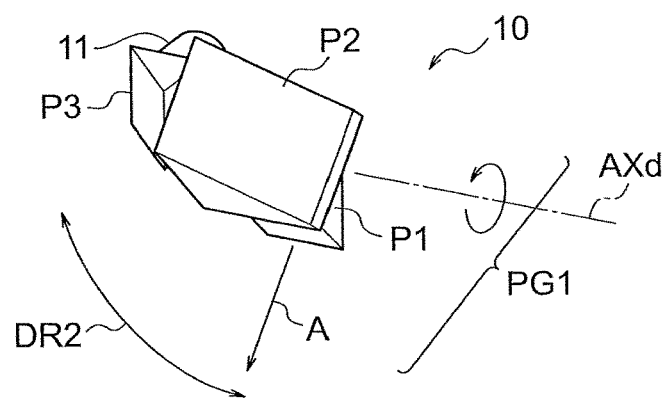
FIG. 1F is still another diagram showing an arrangement in perspective view of the endoscope illuminating optical system according to the first embodiment.
Figure 3A:
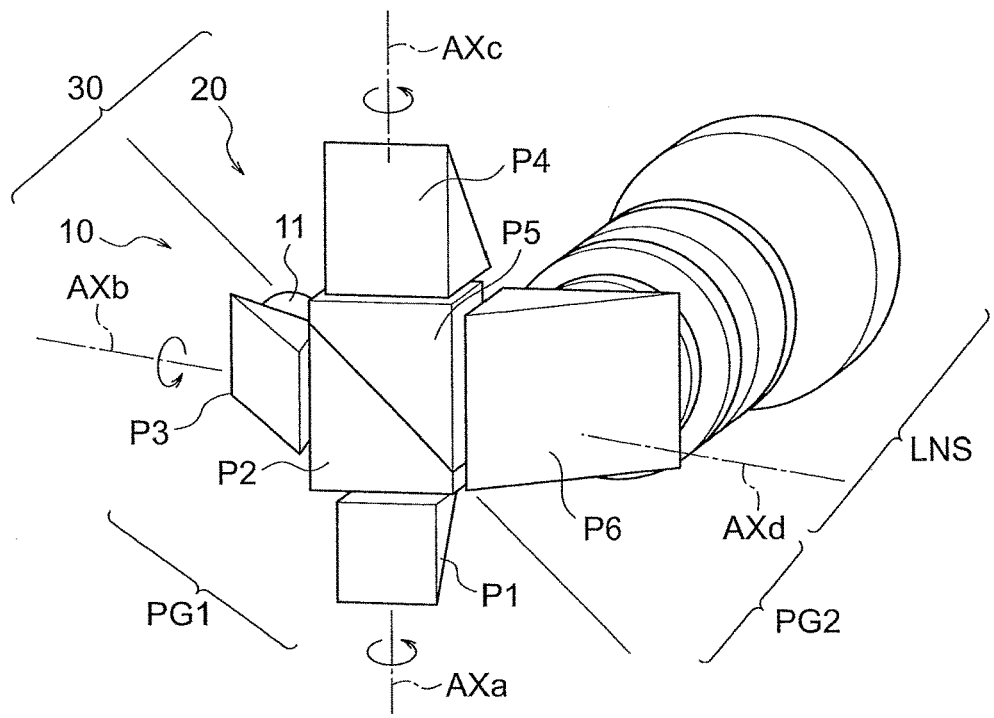
FIG. 3A is a diagram showing an arrangement in perspective view of an endoscope optical system unit according to a third embodiment.
Figure 3B:
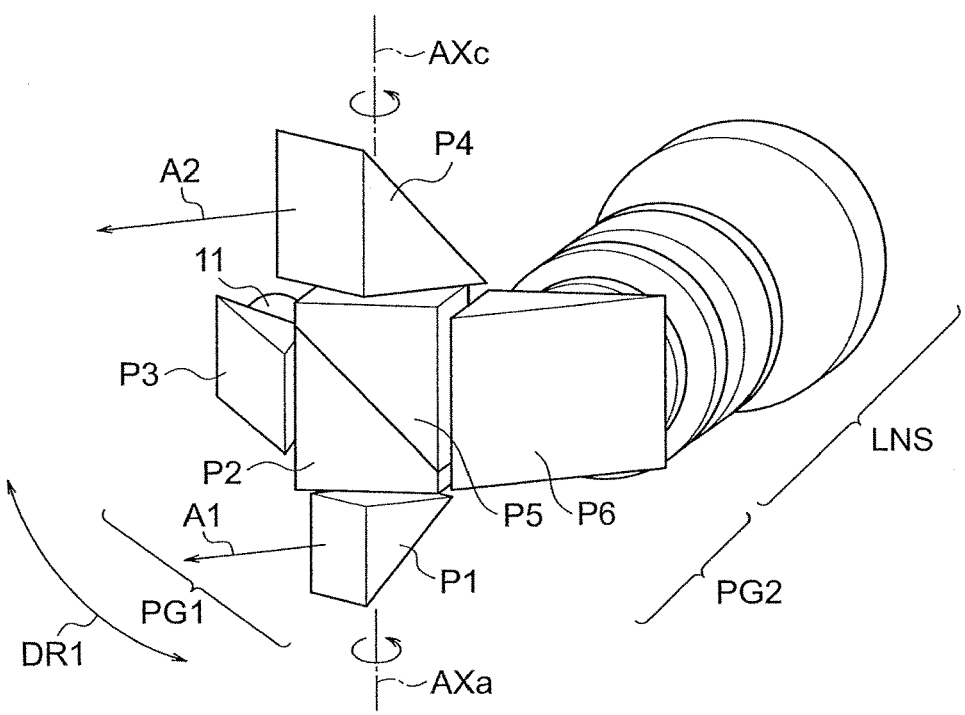
FIG. 3B is another diagram showing an in perspective view of the endoscope optical system unit according to the third embodiment.
Figure 3C:
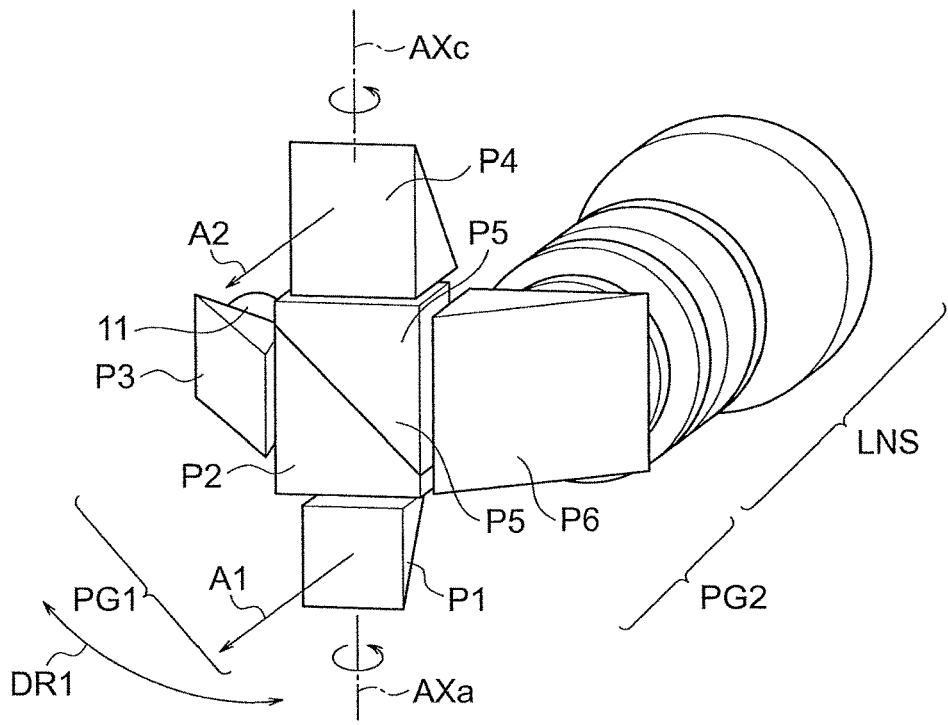
FIG. 3C is still another diagram showing an arrangement in perspective view of the endoscope optical system unit according to the third embodiment.
Figure 3D:
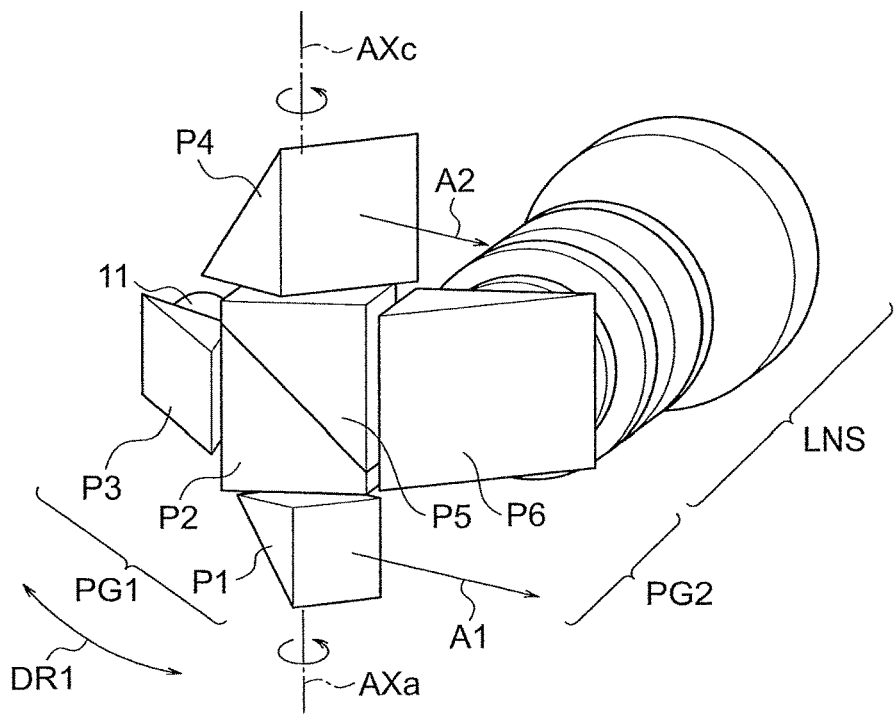
FIG. 3D is still another diagram showing an arrangement in perspective view of the endoscope optical system unit according to the third embodiment.
Figure 3E:
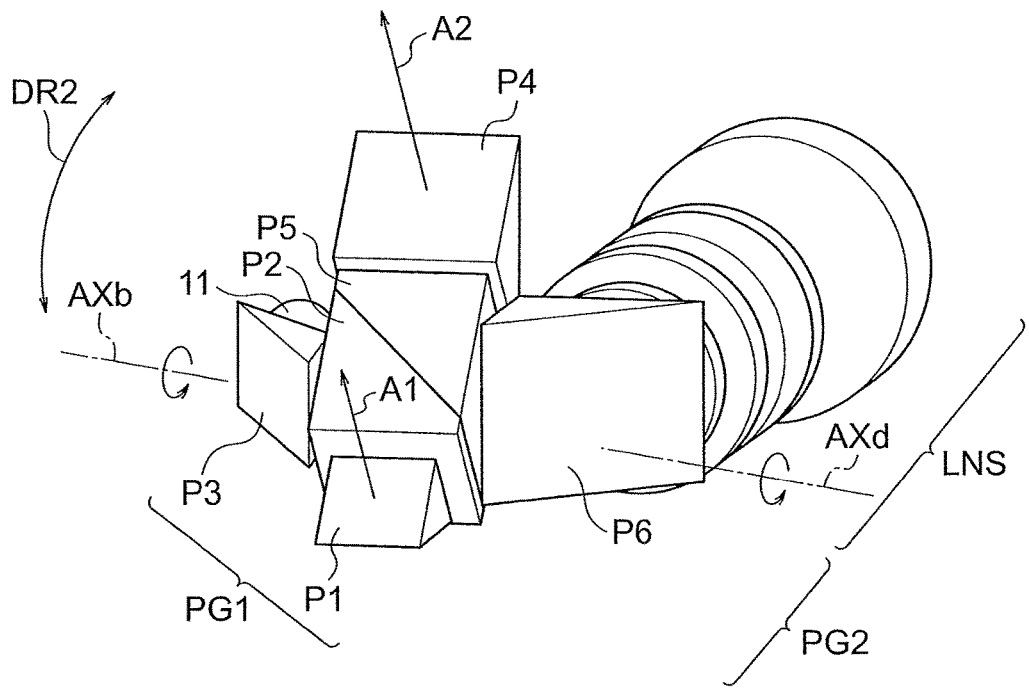
FIG. 3E is still another diagram showing an arrangement in perspective view of the endoscope optical system unit according to the third embodiment.
Figure 3F:
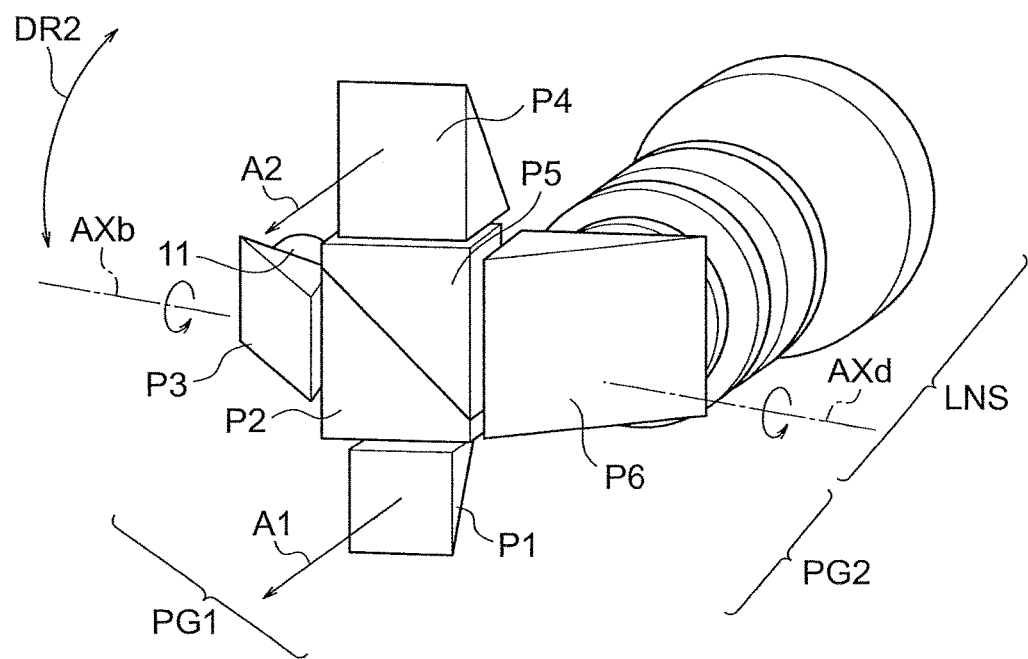
FIG. 3F is still another diagram showing an arrangement in perspective view of the endoscope optical system unit according to the third embodiment.
Figure 3G:
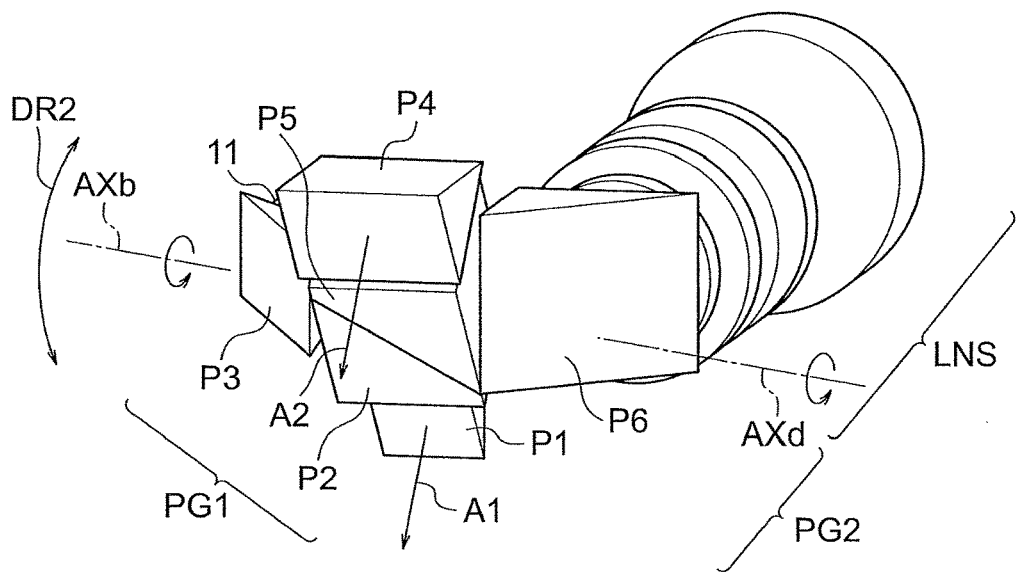
FIG. 3G is a diagram showing an arrangement in perspective view of a modified example of the endoscope optical system unit according to the third embodiment.
Figure 3H:
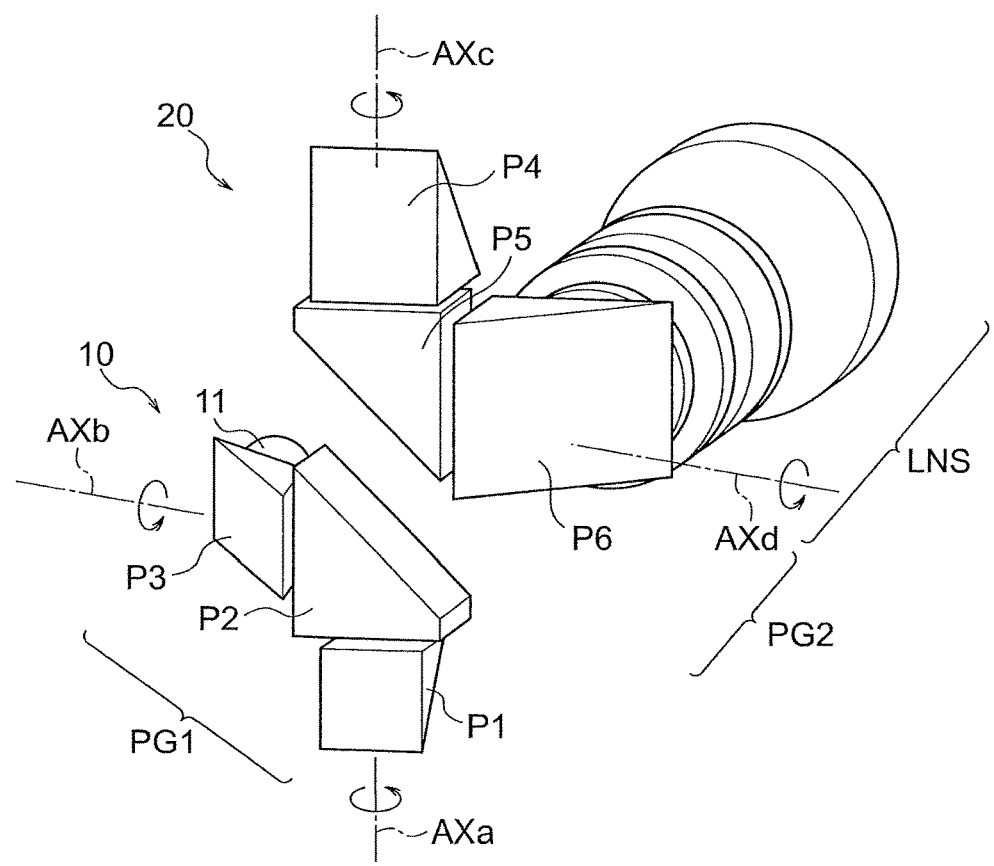
FIG. 3H is still another diagram showing an arrangement in perspective view of the endoscope optical system unit according to the third embodiment.

Reasons for and effects of endoscope illuminating optical system and an endoscope optical system unit according to the present embodiment having such arrangements will be described below by referring to the accompanying diagrams. However, the present invention is not restricted to embodiments described below.

(First Embodiment)

FIG. 1A, FIG. 1B, FIG. 1C, FIG. 1D, FIG. 1E, and FIG. 1F are diagrams showing a schematic arrangement of an endoscope illuminating optical system according to a first embodiment.

An endoscope illuminating optical system 10 includes a light-emitting section 11, and a first optical-path deflecting prism group PG1 which takes in illumination light emitted from the light emitted from the light-emitting section 11, and irradiates light to a subject upon deflecting an optical path. The first optical-path deflecting prism group PG1 includes three prisms in order from the subject side which are, a first prism P1, a second prism P2, and a third prism P3. The first prism P1, the second prism P2, and the third prism P3 are disposed to be mutually adjacent. A direction of irradiation A of the illumination light is let to be variable to a first direction DR1 by rotationally moving the first prism P1 with respect to the second prism P2. Furthermore, the direction of irradiation A of the illumination light is let to be variable to a second direction DR2 which differs from the first direction DR1, by rotationally moving the first prism P1 and the second prism P2 integrally, with respect to the third prism P3.

A light-emitting diode (LED), a laser diode (LD), and a xenon lamp can be used as the light-emitting section 11.

Accordingly, it is possible to change a visual field to an arbitrary direction without bending an endoscope even in a narrow space. Moreover, it is preferable that the first direction DR1 and the second direction DR2 are directions crossing each other at 90 degrees.

A side surface of each of the prisms P1, P2, and P3, which is not an optical surface, can be also painted in black color in advance. Moreover, a reflecting coating may be applied to a reflecting surface of each of the prisms P1, P2, and P3.

(Second Embodiment)

Moreover, according to an endoscope illuminating optical system according to a second embodiment, it is preferable to satisfy conditional expression (1) as shown in FIG. 2. An endoscope objective optical system 20 indicated by dashed lines in FIG. 20, and an endoscope optical system unit 30 will be described later.

$$0.4 \leq L/D \leq 0.6 \quad (1)$$

where,

L denotes a length (unit mm) which is a sum of a length of an optical axis passing through the first prism, a length of an optical axis passing through the second prism, and a length of an optical axis passing through the third prism, and D denotes an outer diameter (unit mm) of an inserting section of an endoscope, in which the endoscope illuminating optical system is built-in.

Conditional expression (1) regulates an appropriate size of the first optical-path deflecting prism group PG1. By satisfying conditional expression (1), it is possible to make small the size of the first optical-path deflecting prism group PG1. Accordingly, it is possible to have an endoscope illuminating optical system built-in inside an inserting section of an endoscope having a small diameter.

When an upper limit value of conditional expression (1) is exceeded, a size of each of the first prism P1, the second prism P2, and the third prism P3 becomes large. Accordingly, a space necessary for a movement of each prism becomes large. Consequently, the endoscope illuminating optical system and an inserting pipe or an endoscope objective optical system that is built-in, interfere. When an amount of movement of each prism is made small in order to avoid such interference, range of variability of the first direction DR1 and the second direction DR2 of the illumination light is reduced.

When a value falls below a lower limit value of conditional expression (1), the size of each of the first prism P1, the second prism P2, and the third prism P3 becomes small. Accordingly, a diameter of a light beam passing through each prism becomes small. As a result, illumination light of adequate brightness cannot be achieved.

(Third Embodiment)

Moreover, an endoscope optical system unit according to a third embodiment, as shown in FIG. 3A, FIG. 3B, FIG. 3C, FIG. 3D, FIG. 3E, FIG. 3F, and FIG. 3G, includes the abovementioned endoscope illuminating optical system 10 and the endoscope objective optical system 20. The endoscope objective optical system 20 includes a second optical-path deflecting prism group PG2 and a lens group LNS. The second optical-path deflecting prism group PG2 includes three prisms in order from a subject side which are, a fourth prism P4, a fifth prism P5, and a sixth prism P6. The fourth prism P4, the fifth prism P5, and the sixth prism P6 are disposed to be mutually adjacent, and a visual-field direction A2 is let to be variable to the first direction DR1 by rotationally moving the fourth prism P4 with respect to the fifth prism P5. The visual-field direction A2 is let to be variable to the second direction DR2 which differs from the first direction DR1, by rotationally moving the two prisms which are, the fourth prism P4 and the fifth prism P5 integrally, with respect to the sixth prism P6. The first optical-path deflecting prism group PG1 and the second optical-path deflecting prism group PG2 are disposed such that a third axis of rotation AXc when the fourth prism P4 rotates with respect to the fifth prism P5, and a first axis of rotation AXa when the first prism P1 of the endoscope illuminating optical system 10 rotates with respect to the second prism P2, become coaxial. The first optical-path deflecting prism group PG1 and the second optical-path deflecting prism group PG2 are disposed such that a fourth axis of rotation AXd when the fourth prism P4 and the fifth prism P5 rotate integrally with respect to the sixth prism P6 and a second axis of rotation AXb when the first prism P1 and the second prism P2 rotate integrally with respect to the third prism P3, become coaxial. Moreover, it is possible to let both the visual-field direction A2 of the endoscope objective optical system 20 and the direction of irradiation A1 of the illumination light of the endoscope illuminating optical system 10 to be variable to the first direction DR1 by rotationally moving the first prism P1 and the fourth prism P4 integrally, and it is possible to let both the visual-field direction A2 of the endoscope objective optical system 20 and the direction of irradiation A1 of the illumination light of the endoscope illuminating optical system 10 to be variable to the second direction DR2 by rotationally moving the first prism P1 and the second prism P2, and the fourth prism P4 and the fifth prism P5 integrally.

According to the present embodiment, with a small-size arrangement, it is possible to move by following the direction of irradiation of the illumination light without delay, with respect to the moving visual-field direction. Accordingly, it is possible to illuminate with uniform and adequate brightness, the visual field achieved by combining the endoscope objective optical system in which the visual field is variable to two directions.

Moreover, in the endoscope optical system unit 30 according to the present embodiment, the second prism P2 of the endoscope illuminating optical system 10 and the fifth prism P5 of the endoscope objective optical system 20 are disposed to be mutually adjacent or in substantially close contact as shown in FIG. 3A to FIG. 3G. However, without restricting to such arrangement, in the endoscope optical system unit 30, an arrangement can also be made such that the endoscope illuminating optical system 10 and the endoscope objective optical system 20 are isolated spatially.

(Fourth Embodiment)

Figure 4:
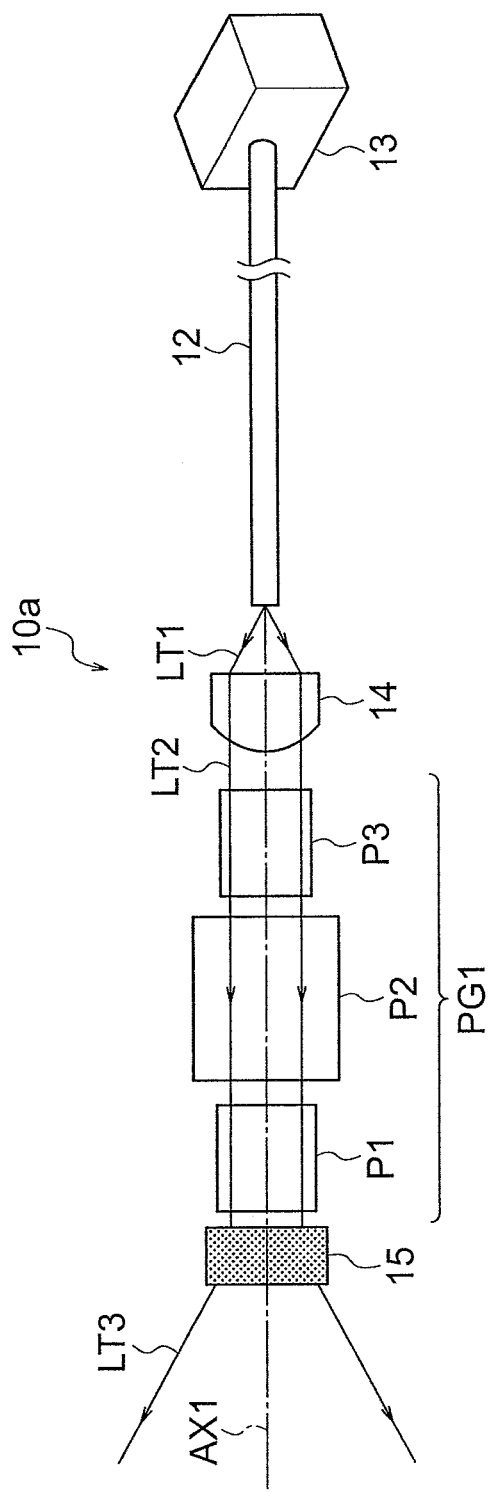
FIG. 4 is a diagram showing an arrangement in cross-sectional view of an endoscope illuminating optical system according to a fourth embodiment.

An endoscope illuminating optical system 10a according to a fourth embodiment, as shown in FIG. 4, includes the light-emitting section 11, a light-source section 13 which irradiates illumination light, and an optical fiber 12 which guides the illumination light from the light-source section 13. Furthermore, the endoscope illuminating optical system 10a includes a collimating optical system 14 and a light diffuser 15. The collimating optical system 14 is disposed in an optical path between the first optical-path deflecting prism group PG1 and the optical fiber 12, and collimates light LT1 emerged from the optical fiber 12. Thereafter, the endoscope illuminating optical system 10a diffuses parallel light LT2 transmitted through the first optical-path deflecting prism group PG1, and irradiates to a subject as diffused light LT3.

Accordingly, it is possible to prevent the illumination light from being vignette by the first prism P1, the second prism P2, and the third prism P3 in the first optical-path deflecting prism group PG1. As a result, it is possible to realize bright illumination efficiently.

(Fifth Embodiment)

Figure 5:
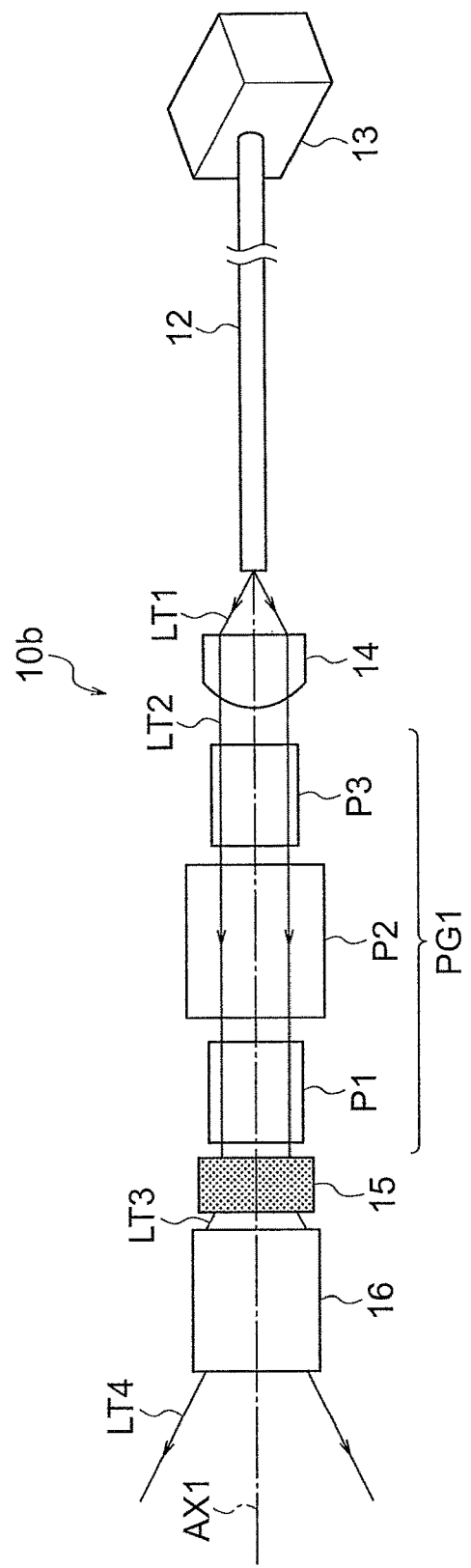
FIG. 5 is a diagram showing an arrangement in cross-sectional view of an endoscope illuminating optical system according to a fifth embodiment.

In an endoscope illuminating optical system 10b according to a fifth embodiment, as shown in FIG. 5, the light-source section 13 is a laser diode light-source unit 13 which emits light of a specific wavelength for example. As mentioned above, a light-emitting diode (LED) and a xenon lamp etc. can also be used as the light-source section 13. Moreover, the endoscope illuminating optical system 10b includes a fluorescent body 16. The fluorescent body 16 is disposed near the light diffuser 15, and emits fluorescent light upon being excited by light of a specific wavelength. The light of specific wavelength is blue laser light. The fluorescent body 16 is for example, a YAG (yttrium aluminum garnet) fluorescent body which emits green fluorescent light. The endoscope illuminating optical system 10b irradiates a subject with white light LT4 which is a mixture of blue light resulted from the blue laser light being diffused by the light diffuser 15 and the green fluorescent light emitted by the fluorescent body 16.

Accordingly, even brighter illumination light is achieved with lesser electric power consumption.

(Sixth Embodiment)

Figure 6:
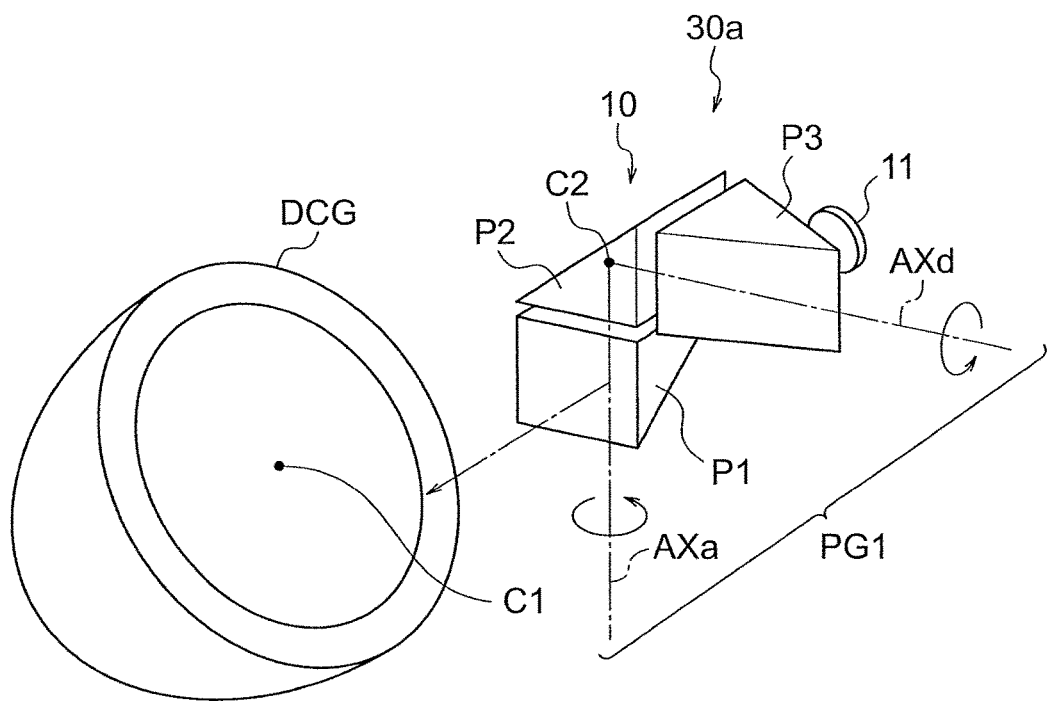
FIG. 6 is a diagram showing an arrangement in perspective view of an endoscope optical system unit according to a sixth embodiment.

In an endoscope optical system unit 30a according to a sixth embodiment, as shown in FIG. 6, a dome-shaped cover glass DCG is disposed between the endoscope illuminating optical system 10 and a subject which is not shown in the diagram. Moreover, a center of curvature C1 of a surface toward the endoscope illuminating optical system 10 of the dome-shaped cover glass DCG, and an intersection point C2 which is a point of intersection of the first axis of rotation AXa and the second axis of rotation AXb, coincide.

Accordingly, the first prism P1 which moves in a space at an inner side of the dome-shaped cover glass DCG and the dome-shaped cover glass DCG can maintain same positional relationship in any state during the rotation of the first prism P1. As a result, it is possible to prevent interference of the first prism P1 and the dome-shape cover glass DCG while taking a wide range of variability of the direction of irradiation of the illumination light.

(Seventh Embodiment)

Figure 7:
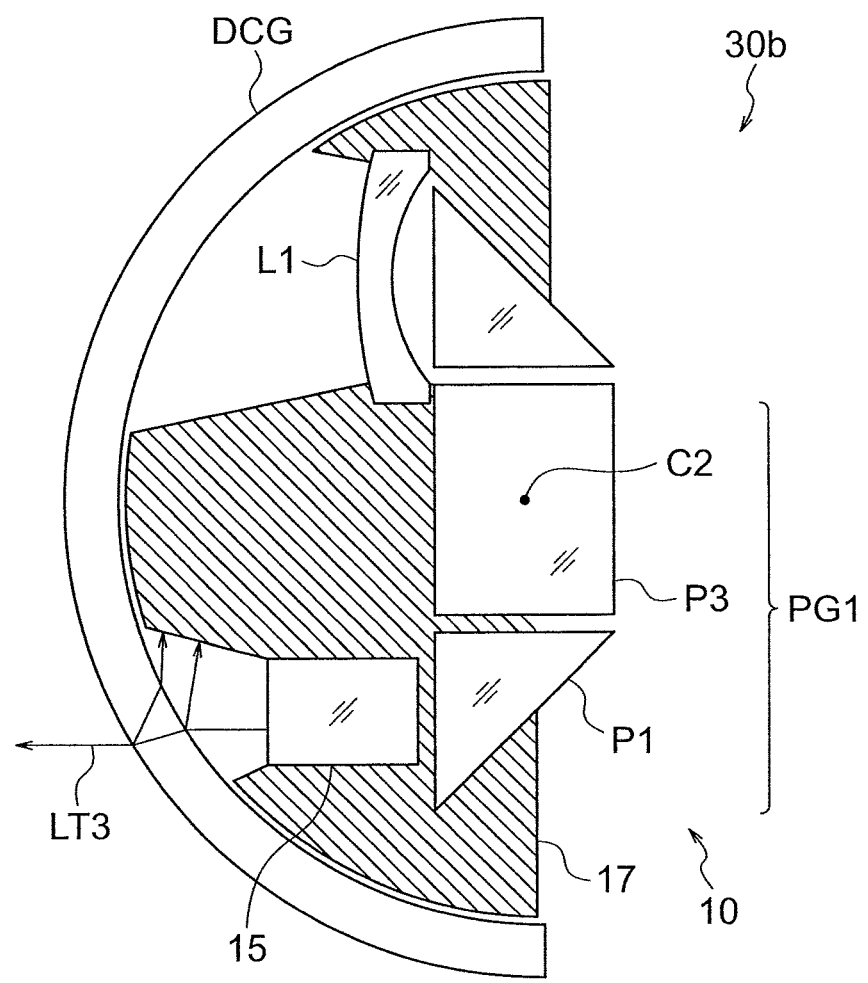
FIG. 7 is a diagram showing an arrangement in cross-sectional view of an endoscope optical system unit according to a seventh embodiment.

An endoscope optical system unit 30b according to a seventh embodiment, as shown in FIG. 7, includes a light-shielding member 17 which encloses a space on an outer side of a range through which the illumination light irradiated from the endoscope illuminating optical system 10 is transmitted, out of an inner-side space toward the endoscope illumination optical system 10, of the dome-shaped cover glass. In FIG. 7, a light-shielding area is indicated by oblique lines. It is desirable that the light-shielding member 17 move integrally with the first prism P1 which undergoes rotational movement for changing the direction of irradiation of the illumination light.

Accordingly, the light-shielding member 17 cuts off the illumination light reflected at an inner-side surface of the dome-shaped cover glass DCG. As a result, it is possible to prevent unnecessary light from being incident on the endoscope objective optical system and causing flare and ghost.

Next, examples and numerical examples of the endoscope illuminating optical system and the endoscope optical system unit will be described below.

EXAMPLE 1

Figure 8:
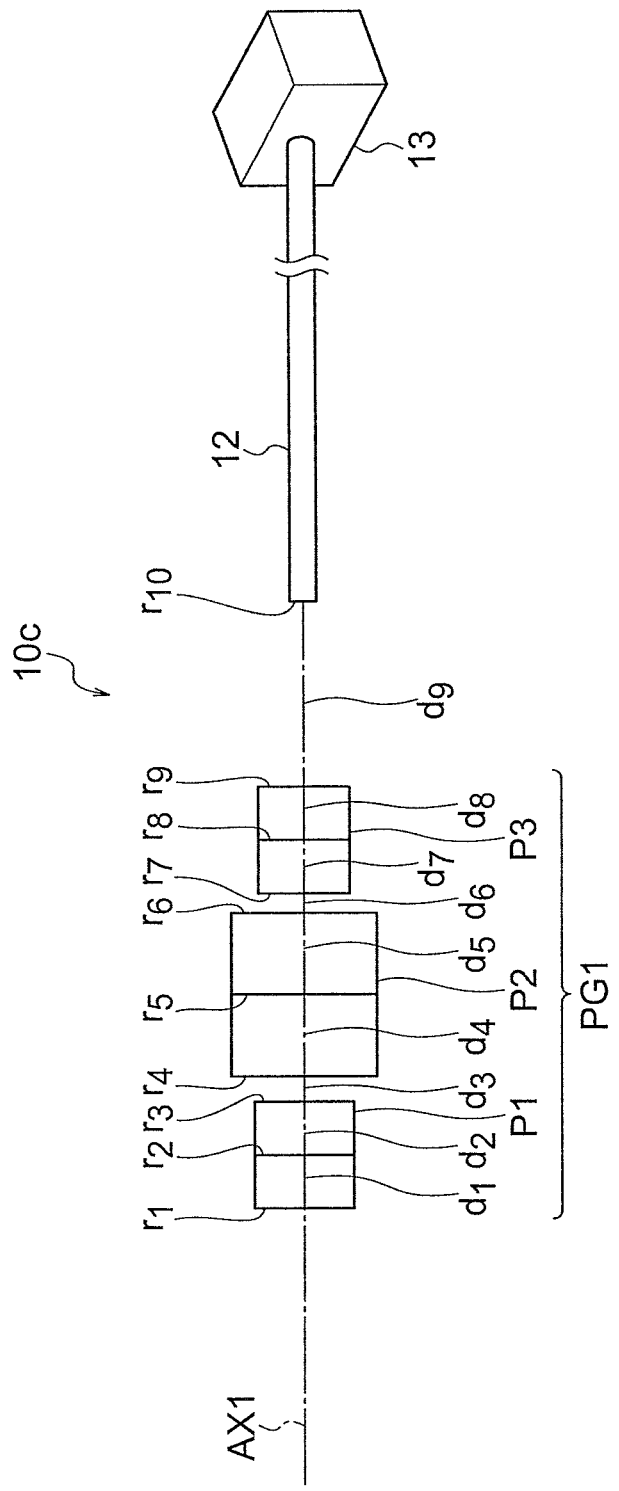
FIG. 8 is a diagram showing an arrangement in cross-sectional view of an endoscope illuminating optical system according to an example 1.

FIG. 8 is a cross-sectional view showing an arrangement of an endoscope illuminating optical system 10c according to an example 1. In FIG. 8, the prism P1, the prism P2, and the prism P3 are shown to be developed. Therefore, the prisms are depicted as plane parallel plates.

The endoscope illuminating optical system 10c according to the example 1 includes in order from a subject (an object) side, the first optical-path deflecting prism group PG1, the optical fiber 12, and the laser diode light-source unit 13. The first optical-path deflecting prism group PG1 includes the first prism P1, the second prism P2, and the third prism P3.

EXAMPLE 2

FIG. 9A is a cross-sectional view showing an arrangement of an endoscope illuminating optical system 10d in an endoscope optical system unit according to an example 2. In FIG. 9A, the prism P1, the prism P2, and the prism P3 are shown to be developed. Therefore, the prisms are depicted as plane parallel plates.

The endoscope illuminating optical system 10d according to the example 2 includes in order from a subject (an object) side, the first optical-path deflecting prism group PG1, the optical fiber 12, and the laser diode light-source unit 13. The first optical-path deflecting prism group PG1 includes the first prism P1, the second prism P2, and the third prism P3.

Figure 9B:
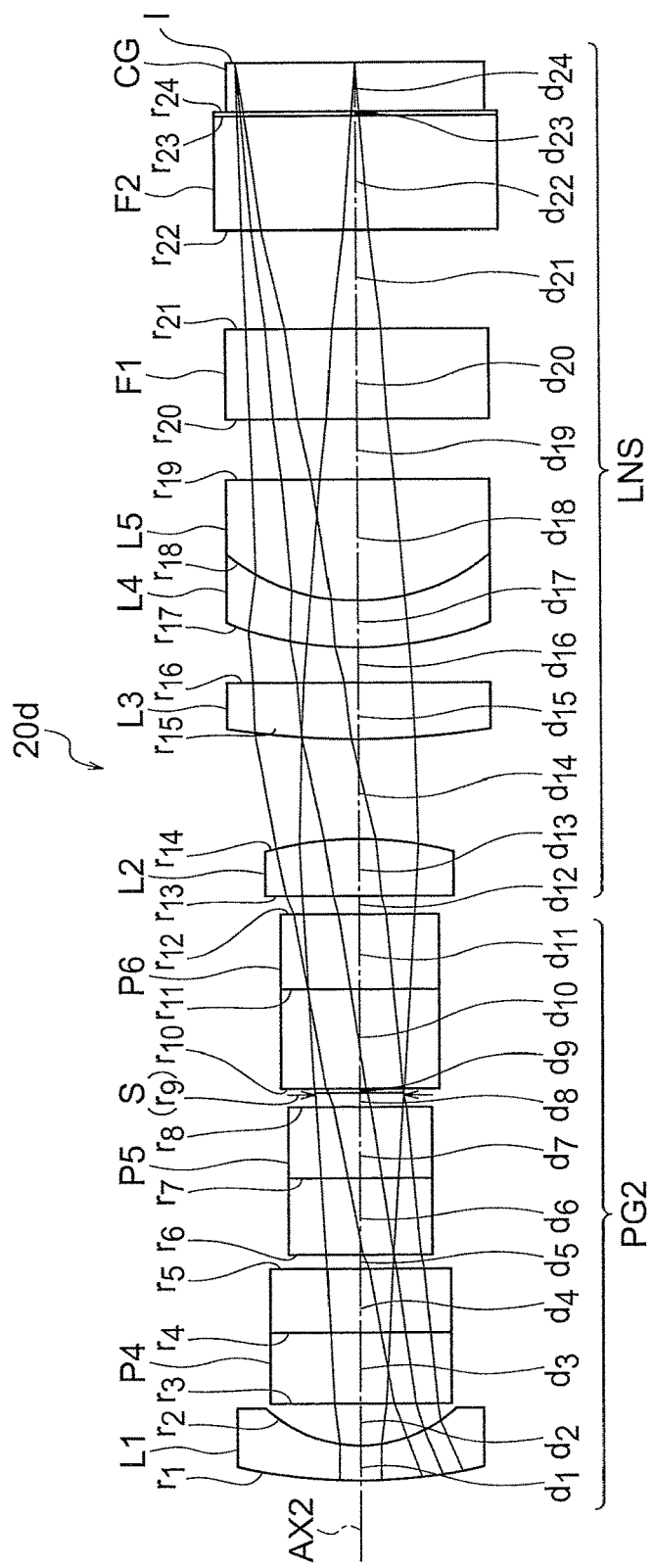
FIG. 9B is a diagram showing an arrangement in cross-sectional view of an endoscope objective optical system included in the endoscope optical system unit according to the example 2.

FIG. 9B is a cross-sectional view showing an arrangement of an endoscope objective optical system 20d in the endoscope optical system unit according to the example 2. In FIG. 9B, the fourth prism P4, the fifth prism P5, and the sixth prism P6 are shown to be developed. Therefore, the prisms are depicted as plane parallel plates.

The endoscope objective optical system 20d in the endoscope optical system unit according to the example 2 includes in order from a subject (an object) side, the second optical-path deflecting prism group PG2 and the lens group LNS. The second optical-path deflecting prism group PG2 includes a negative meniscus lens L1 having a convex surface directed toward the object side, the fourth prism P4, the fifth prism P5, and the sixth prism P6. The lens group LNS includes a planoconvex positive lens L2 having a convex surface directed toward an image-plane side, a planoconvex positive lens L3 having a convex surface directed toward the object side, a negative meniscus lens L4 having a convex surface directed toward the object side, a planoconvex positive lens L5 having a convex surface directed toward the object side, a plane parallel plate F1, a plane parallel plate F2, and a plane parallel plate CG. The negative meniscus lens L4 and the planoconvex positive lens L5 are cemented. There is a cemented layer between the plane parallel plate F2 and the plane parallel plate CG.

The plane parallel plate F1 is an infra-red absorbing filter.

EXAMPLE 3

Figure 10:
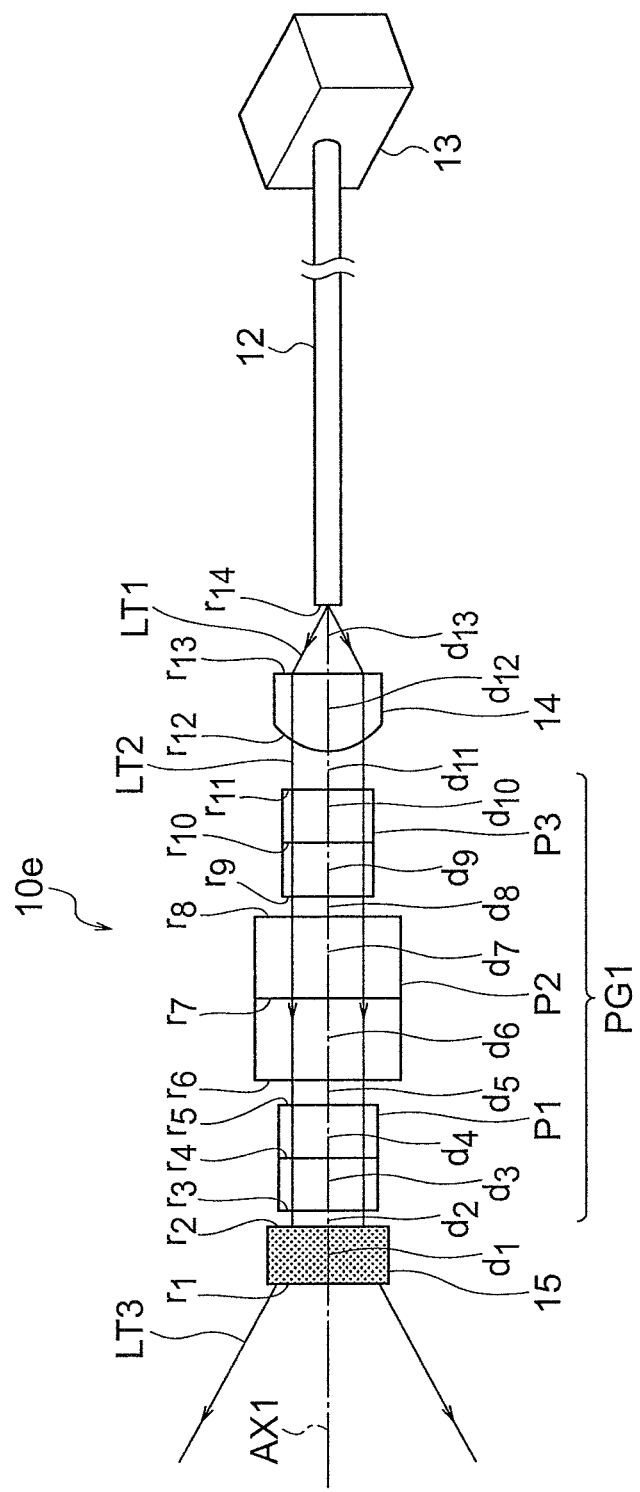
FIG. 10 is a diagram showing an arrangement in cross-sectional view of an endoscope illuminating optical system according to an example 3.

FIG. 10 is a cross-sectional view showing an arrangement of an endoscope illuminating optical system 10e according to an example 3. In FIG. 10, the prism P1, the prism P2, and the prism P3 are shown to be developed. Therefore, the prisms are depicted as plane parallel plates.

The endoscope illuminating optical system 10e according to the example 3 includes in order from an object side, the light diffuser 15, the first optical-path deflecting prism group PG1, the collimating optical system 14, the optical fiber 12, and the laser diode light-source unit 13. The first optical-path deflecting prism group PG1 includes the first prism P1, the second prism P2, and the third prism P3.

EXAMPLE 4

Figure 11:
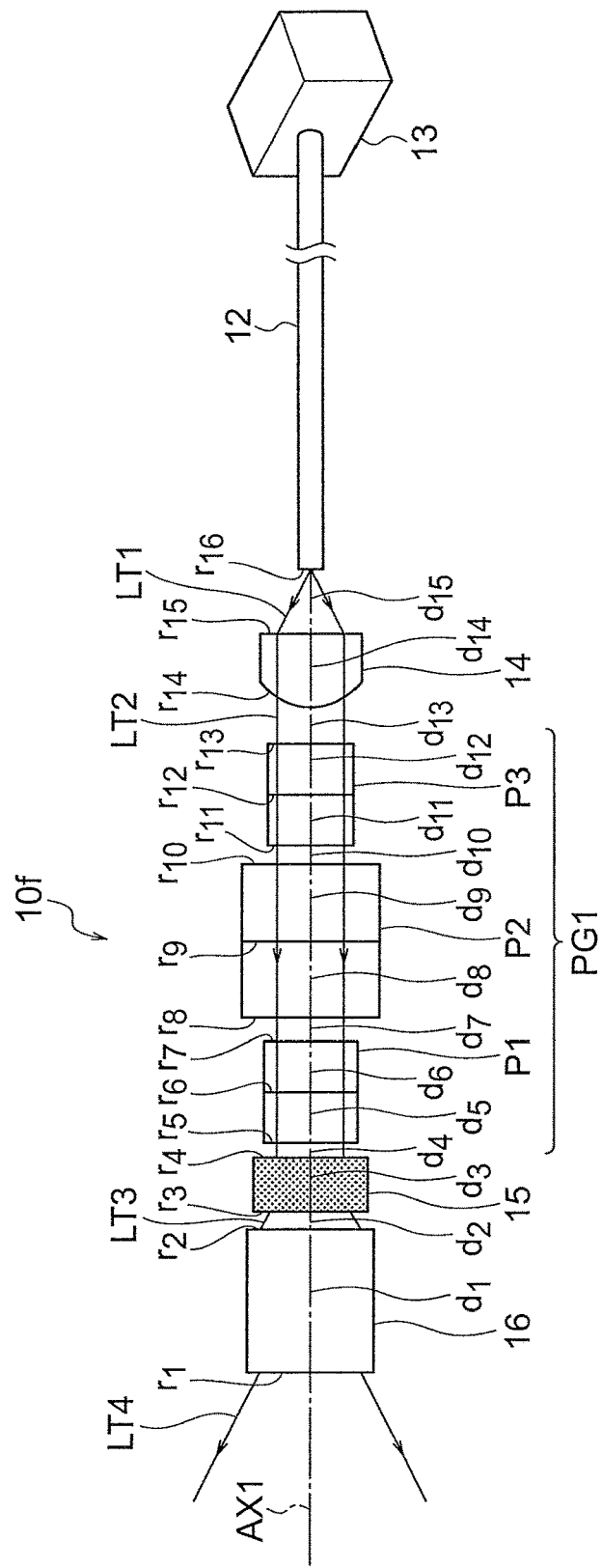
FIG. 11 is a diagram showing an arrangement in cross-sectional view of an endoscope illuminating optical system according to an example 4.

FIG. 11 is a cross-sectional view showing an arrangement of an endoscope illuminating optical system 10f according to an example 4. In FIG. 11, the prism P1, the prism P2, and the prism P3 are shown to be developed. Therefore, the prisms are depicted as plane parallel plates.

The endoscope illuminating optical system 10f according to the example 4 includes in order from the object side, the fluorescent body 16, the light diffuser 15, the first optical-path deflecting prism group PG1, the optical fiber 12, and the laser diode light-source unit 13. The first optical-path deflecting prism group PG1 includes the first prism P1, the second prism P2, and the third prism P3.

EXAMPLE 5

Figure 12:
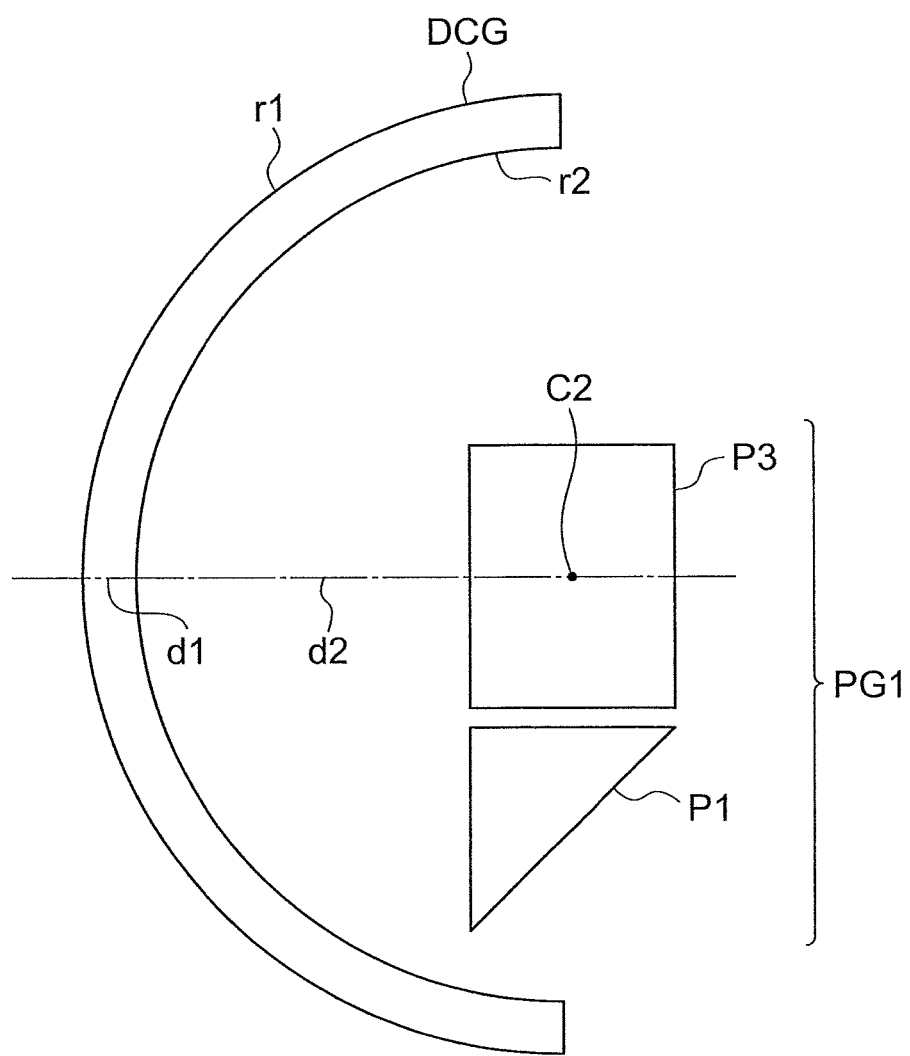
FIG. 12 is a diagram showing an arrangement in cross-sectional view of a dome-shaped cover glass of an endoscope optical system unit according to an example 5.

FIG. 12 is a cross-sectional view showing an arrangement near the dome-shaped cover glass DCG of an endoscope optical system unit according to an example 5.

The dome-shaped cover glass DCG is a bowl-shaped member, and both an object-side surface and an image-side surface thereof are curved surfaces. In FIG. 12, since both the object-side surface and the image-side surface being spherical surfaces having the same center of curvature, an overall shape of the dome-shaped cover glass DCG is hemispherical. In the present example, a thickness of the dome-shaped cover glass, or in other words, a spacing between the object-side surface and the image-side surface is constant in a direction toward the center of curvature.

The dome-shaped cover glass DCG functions as a cover glass. In this case, the dome-shaped cover glass DCG corresponds to an observation window provided to an outer covering section of a capsule endoscope. Therefore, the optical systems of examples 1 to 4 can be used for an optical system of a capsule endoscope.

Numerical data for each example is shown below. In surface data, r denotes a radius of curvature of each lens surface, d denotes a distance between lens surfaces, nd denotes a refractive index for d-line of each lens, and νd denotes Abbe's number for each lens. Further, RS denotes reflection surface.

EXAMPLE 1

Unit mm
(Endoscope illuminating optical system)
Surface data

| Surface no. | r | d | nd | νd |
|---|---|---|---|---|
| 1 | ∞ | 0.35 | 2.0033 | 28.27 |
| 2 | ∞ (RS) | 0.35 | 2.0033 | 28.27 |
| 3 | ∞ | 0.15 | | |
| 4 | ∞ | 0.55 | 2.0033 | 28.27 |
| 5 | ∞ (RS) | 0.55 | 2.0033 | 28.27 |
| 6 | ∞ | 0.15 | | |
| 7 | ∞ | 0.35 | 2.0033 | 28.27 |
| 8 | ∞ (RS) | 0.35 | 2.0033 | 28.27 |
| 9 | ∞ | 0.5 | | |
| 10 | ∞ (End surface of optical fiber) | | | |

EXAMPLE 2

Unit mm
(Endoscope illuminating optical system for endoscope optical system unit)
Surface data

| Surface no. | r | d | nd | νd |
|---|---|---|---|---|
| 1 | ∞ | 0.35 | 2.0033 | 28.27 |
| 2 | ∞ (RS) | 0.35 | 2.0033 | 28.27 |
| 3 | ∞ | 0.1 | | |
| 4 | ∞ | 0.55 | 2.0033 | 28.27 |
| 5 | ∞ (RS) | 0.5 | 2.0033 | 28.27 |
| 6 | ∞ | 0.1 | | |
| 7 | ∞ | 0.35 | 2.0033 | 28.27 |
| 8 | ∞ (RS) | 0.35 | 2.0033 | 28.27 |
| 9 | ∞ | 0.1 | | |
| 10 | ∞ (End face of optical fiber) | | | |

(Endoscope illuminating optical system for endoscope optical system unit)
Surface data

| Surface no. | r | d | nd | νd |
|---|---|---|---|---|
| Object plane | ∞ | 19.08 | | |
| 1 | 4.054158 | 0.25 | 1.8830 | 40.77 |
| 2 | 0.9812464 | 0.299 | | |
| 3 | ∞ | 0.5 | 2.0033 | 28.27 |
| 4 | ∞ | 0.45 | 2.0033 | 28.27 |
| 5 | ∞ | 0.1 | | |
| 6 | ∞ | 0.55 | 2.0033 | 28.27 |
| 7 | ∞ | 0.5 | 2.0033 | 28.27 |
| 8 | ∞ | 0.1 | | |
| 9 (Stop) | ∞ | 0.03 | | |
| 10 | ∞ | 0.697 | 2.0033 | 28.27 |
| 11 | ∞ | 0.543 | 2.0033 | 28.27 |
| 12 | ∞ | 0.13 | | |
| 13 | ∞ | 0.4 | 1.7859 | 44.20 |
| 14 | −2.458494 | 0.7 | | |
| 15 | 5.909847 | 0.4 | 1.8830 | 40.77 |
| 16 | ∞ | 0.249 | | |
| 17 | 2.726864 | 0.32 | 1.9229 | 18.90 |
| 18 | 1.482493 | 0.85 | 1.4970 | 81.55 |
| 19 | ∞ | 0.43 | | |
| 20 | ∞ | 0.62 | 1.5140 | 75.00 |
| 21 | ∞ | 0.7 | | |
| 22 | ∞ | 0.8 | 1.5163 | 64.14 |
| 23 | ∞ | 0.02 | 1.5100 | 63.80 |
| 24 | ∞ | 0.35 | 1.6135 | 50.20 |
| Image pickup surface | ∞ | | | |

Various data

| | |
|---|---|
| FL | 1.376 mm |
| L | 10 mm |
| Fno | 4.46 |
| 2ω | 70° |

EXAMPLE 3

Unit mm
(Endoscope illuminating optical system)
Surface data

| Surface no. | r | d | nd | νd |
|---|---|---|---|---|
| 1 | ∞ | 0.3 | Light diffuser | |
| 2 | ∞ | 0.1 | | |
| 3 | ∞ | 0.35 | 2.0033 | 28.27 |
| 4 | ∞ (RS) | 0.35 | 2.0033 | 28.27 |
| 5 | ∞ | 0.1 | | |
| 6 | ∞ | 0.55 | 2.0033 | 28.27 |
| 7 | ∞ (RS) | 0.5 | 2.0033 | 28.27 |
| 8 | ∞ | 0.1 | | |
| 9 | ∞ | 0.35 | 2.0033 | 28.27 |
| 10 | ∞ (RS) | 0.35 | 2.0033 | 28.27 |
| 11 | ∞ | 0.1 | | |
| 12 | 0.475 | 0.58 | 1.883 | 40.77 |
| 13 | ∞ | 0.21 | | |
| 14 | ∞ (End face of optical fiber) | | | |

EXAMPLE 4

Unit mm
(Endoscope illuminating optical system)
Surface data

| Surface no. | r | d | nd | νd |
|---|---|---|---|---|
| 1 | ∞ | 0.7 | Fluorescent body | |
| 2 | ∞ | 0.05 | | |
| 3 | ∞ | 0.3 | Light diffuser | |
| 4 | ∞ | 0.1 | | |
| 5 | ∞ | 0.35 | 2.0033 | 28.27 |
| 6 | ∞ (RS) | 0.35 | 2.0033 | 28.27 |
| 7 | ∞ | 0.1 | | |
| 8 | ∞ | 0.55 | 2.0033 | 28.27 |
| 9 | ∞ (RS) | 0.5 | 2.0033 | 28.27 |
| 10 | ∞ | 0.1 | | |
| 11 | ∞ | 0.35 | 2.0033 | 28.27 |
| 12 | ∞ (RS) | 0.35 | 2.0033 | 28.27 |
| 13 | ∞ | 0.1 | | |
| 14 | 0.475 | 0.58 | 1.883 | 40.77 |
| 15 | ∞ | 0.21 | | |
| 16 | ∞ (End face of optical fiber) | | | |

EXAMPLE 5

Unit mm (Doom cover glass for endoscope illuminating optical system)
Surface data

| Surface no. | r | d | nd | vd |
|---|---|---|---|---|
| 1 | 2.7 | 0.3 | 1.7682 | 72.2 |
| 2 | 2.4 | 2.4 | | |
| 3 (Center of curvature) | | | | |

Values of the conditional expression are shown below,
where L = L1 + L2 + L3

| conditional expression | ex6 | modified ex6 | another modified ex6 |
|---|---|---|---|
| D | 5.4 | 5.4 | 5.4 |
| L1 | 0.56 | 0.7 | 1.07 |
| L2 | 1.05 | 1.05 | 1.1 |
| L3 | 0.56 | 1.0 | 1.0 |
| (1) L/D | 0.402 | 0.509 | 0.60 |

As described above, according to the present invention, it is possible to provide an endoscope illuminating optical system which enables to change a direction of irradiation of illumination light to two directions without bending an endoscope even in a narrow space. Moreover, according to the present invention, it is possible to provide an endoscope optical system unit which enables to illuminate with uniform and adequate brightness, the visual field achieved by combining with an endoscope objective optical system in which the visual field is variable to two directions.

Various embodiments of the present embodiment have been described above. However, the present invention is not limited only two these embodiments, and embodiments in which the arrangements of the abovementioned embodiments have been combined appropriately without departing from the scope of the invention also fall under the category of the present invention.

As describe above, the present invention is useful for an endoscope illuminating optical system which enables to change a direction of irradiation of illumination light to two directions without bending an endoscope even in a narrow space, and for an endoscope optical system unit which enables to illuminate with uniform and adequate brightness, the visual field achieved by combining with an endoscope objective optical system in which the visual field is variable to two directions.

The present invention shows an effect that it is possible to provide an endoscope illuminating optical system which enables to change a direction of irradiation of illumination light to two directions without bending an endoscope even in a narrow space. Moreover, the present invention shows an effect that it is possible to provide an endoscope optical system unit which enables to illuminate with uniform and adequate brightness, the visual field achieved by combining with an endoscope objective optical system in which the visual field is variable to two directions.

What is claimed is:

1. An endoscope optical system unit, comprising:
   (i) an endoscope illuminating optical system which includes:
      a light source that irradiates illumination light, and
      a first optical-path deflecting prism group which takes in the illumination light emitted from the light source, deflects the illumination light, and irradiates the deflected light to a subject,
   wherein:
      the first optical-path deflecting prism group includes three prisms in order from a subject side which are a first prism, a second prism, and a third prism,
      the first prism, the second prism, and the third prism are disposed to be mutually adjacent,
      a direction of irradiation of the illumination light is variable in a first direction by rotationally moving the first prism with respect to the second prism, and
      the direction of irradiation of the illumination light is variable in a second direction which differs from the first direction, by rotationally moving the first prism and the second prism integrally, with respect to the third prism; and
   (ii) an endoscope objective optical system which includes:
      a second optical-path deflecting prism group, and
      a lens group,
   wherein:
      the second optical-path deflecting prism group includes three prisms in order from the subject side which are a fourth prism, a fifth prism, and a sixth prism,
      the fourth prism, the fifth prism, and the sixth prism are disposed to be mutually adjacent,
      a visual field direction is variable in the first direction by rotationally moving the fourth prism with respect to the fifth prism,
      the visual field direction is variable in the second direction which differs from the first direction, by rotationally moving the fourth prism and the fifth prism integrally, with respect to the sixth prism,
   wherein the first optical-path deflecting prism group and the second optical-path deflecting prism group are disposed such that a third axis of rotation when the fourth prism rotates with respect to the fifth prism, and a first axis of rotation when the first prism rotates with respect to the second prism, are coaxial,
   wherein the first optical-path deflecting prism group and the second optical-path deflecting prism group are disposed such that a fourth axis of rotation when the fourth prism and the fifth prism rotate integrally with respect to the sixth prism, and a second axis of rotation when the first prism and the second prism rotate integrally with respect to the third prism, are coaxial, and
   wherein both the visual field direction of the endoscope objective optical system and the direction of irradiation of the illumination light of the endoscope illuminating optical system are variable in the first direction by rotationally moving the first prism and the fourth prism integrally, and both the visual field direction of the endoscope objective optical system and the direction of irradiation of the illumination light of the endoscope illuminating optical system are variable in the second direction by rotationally moving the first prism, the second prism, the fourth prism, and the fifth prism integrally.

2. The endoscope optical system unit according to claim 1, wherein a dome-shaped cover glass is disposed between the endoscope illuminating optical system and the subject, and a center of curvature of a surface toward the endoscope illuminating optical system, of the dome-shaped cover glass and a point of intersection of the first axis of rotation and the second axis of rotation coincide.

3. The endoscope optical system unit according to claim 2, further comprising:

a light shield which cuts off the illumination light reflected at an inner-side surface of the dome-shaped cover glass and which encloses a space on an outer side of a range of the dome-shaped cover glass through which the illumination light irradiated from the endoscope illuminating optical system is transmitted, wherein the light shield is provided at an inner-side space of the dome-shaped cover glass, with respect to the endoscope illuminating optical system, and wherein the light shield and the first prism move integrally.

* * * * *